United States Patent
Limbach et al.

(10) Patent No.: US 10,829,431 B2
(45) Date of Patent: Nov. 10, 2020

(54) METHOD FOR PRODUCTION OF METHYL METHACRYLATE BY OXIDATIVE ESTERIFICATION USING A HETEROGENEOUS CATALYST

(71) Applicants: Dow Global Technologies LLC, Midland, MI (US); Rohm and Haas Company, Collegeville, PA (US)

(72) Inventors: Kirk W. Limbach, Dresher, PA (US); Dmitry A. Krapchetov, Lansdale, PA (US); Christopher D. Frick, Pottstown, PA (US); Daniel A. Hickman, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/632,939

(22) PCT Filed: Jun. 25, 2018

(86) PCT No.: PCT/US2018/039238
§ 371 (c)(1),
(2) Date: Jan. 22, 2020

(87) PCT Pub. No.: WO2019/022889
PCT Pub. Date: Jan. 31, 2019

(65) Prior Publication Data
US 2020/0148620 A1  May 14, 2020

Related U.S. Application Data

(60) Provisional application No. 62/538,237, filed on Jul. 28, 2017.

(51) Int. Cl.
*C07C 67/39* (2006.01)
*C07C 69/54* (2006.01)

(52) U.S. Cl.
CPC .............. *C07C 67/39* (2013.01); *C07C 69/54* (2013.01); *C07C 2521/04* (2013.01); *C07C 2521/06* (2013.01); *C07C 2523/44* (2013.01); *C07C 2523/52* (2013.01)

(58) Field of Classification Search
CPC ......... C07C 67/39; C07C 45/75; C07C 69/54; B01J 23/89; B01J 23/44
See application file for complete search history.

(56) References Cited

U.S. PATENT DOCUMENTS

| | | |
|---|---|---|
| 4,249,019 A | 2/1981 | Tamura et al. |
| 4,518,796 A | 5/1985 | Aoshima et al. |
| 4,520,125 A | 5/1985 | Baer et al. |
| 5,892,102 A | 4/1999 | Mikami et al. |
| 5,969,178 A | 10/1999 | Okamoto et al. |
| 6,040,472 A | 3/2000 | Yamamatsu et al. |
| 6,107,515 A | 8/2000 | Yamaguchi et al. |
| 6,228,800 B1 | 5/2001 | Yamaguchi et al. |
| 6,348,619 B1 | 2/2002 | Yoshida et al. |
| 7,326,806 B2 | 2/2008 | Hayashi et al. |
| 8,461,373 B2 | 6/2013 | Suzuki et al. |
| 8,614,349 B2 | 12/2013 | Yokota et al. |
| 9,511,351 B2 | 12/2016 | Feaviour |
| 9,617,199 B2 | 4/2017 | Krill et al. |
| 2010/0249448 A1 | 9/2010 | Suzuki et al. |
| 2016/0251301 A1 | 9/2016 | Krill et al. |
| 2016/0280628 A1 | 9/2016 | Krill et al. |
| 2018/0001307 A1 | 1/2018 | Lygin et al. |
| 2018/0326400 A1 | 11/2018 | Lygin et al. |
| 2019/0099731 A1* | 4/2019 | Lygin ...................... B01J 8/226 |

FOREIGN PATENT DOCUMENTS

| | | |
|---|---|---|
| CN | 1931824 | 3/2007 |
| JP | 2003048863 | 2/2003 |
| WO | 2015091173 | 6/2015 |
| WO | 2016113106 | 7/2016 |
| WO | 2017084969 | 5/2017 |

OTHER PUBLICATIONS

Weekman, Jr. et al., Aiche J, 1974, 20, p. 835.

* cited by examiner

*Primary Examiner* — Jafar F Parsa
(74) *Attorney, Agent, or Firm* — Brian L. Mutscher

(57) ABSTRACT

A method for preparing methyl methacrylate from methacrolein and methanol. The method comprises contacting in a reactor a mixture comprising methacrolein, methanol and oxygen with a heterogeneous catalyst comprising a support and a noble metal, wherein said catalyst has an average diameter of at least 200 microns, wherein oxygen concentration at a reactor outlet is from 0.5 to 7.5 mol % and wherein the reactor comprises a partition with the catalyst bed on a first side of the partition and with flow through the catalyst bed in a first direction and flow on a second side of the partition in an opposite direction.

9 Claims, No Drawings

US 10,829,431 B2

METHOD FOR PRODUCTION OF METHYL METHACRYLATE BY OXIDATIVE ESTERIFICATION USING A HETEROGENEOUS CATALYST

BACKGROUND OF THE INVENTION

The invention relates to a method for preparing methyl methacrylate from methacrolein and methanol using a heterogeneous catalyst.

Processes using heterogeneous catalysts having noble metals in oxidative esterification reactions in continuous stirred tank reactors are known, see, e.g., U.S. Pat. No. 6,228,800. However, there is a need for a process which can provide improved performance.

SUMMARY OF THE INVENTION

The present invention is directed to a method for preparing methyl methacrylate from methacrolein and methanol; said method comprising contacting in a reactor a mixture comprising methacrolein, methanol and oxygen with a catalyst bed comprising a heterogeneous catalyst comprising a support and a noble metal, wherein said catalyst has an average diameter of at least 200 microns, wherein oxygen concentration at a reactor outlet is from 0.5 to 7.5 mol %, and wherein the reactor comprises a partition with the catalyst bed on a first side of the partition and with flow through the catalyst bed in a first direction and flow on a second side of the partition in an opposite direction.

DETAILED DESCRIPTION OF THE INVENTION

All percentage compositions are weight percentages (wt %), and all temperatures are in ° C., unless otherwise indicated. A noble metal is any of gold, platinum, iridium, osmium, silver, palladium, rhodium and ruthenium. More than one noble metal may be present in the catalyst, in which case the limits apply to the total of all noble metals. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Preferably, the support is a particle of an oxide material; preferably γ-, δ-, or θ-alumina, silica, magnesia, titania, zirconia, hafnia, vanadia, niobium oxide, tantalum oxide, ceria, yttria, lanthanum oxide or a combination thereof; preferably titania or γ-, δ-, or θ-alumina. Preferably, in portions of the catalyst comprising noble metal, the support has a surface area greater than 50 m$^2$/g, preferably greater than 100 m$^2$/g, preferably greater than 120 m$^2$/g. In portions of the catalyst which comprise little or no noble metal, the support may have a surface area with less than 50 m$^2$/g, preferably less than 20 m$^2$/g.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the catalyst particle include spheres, cylinders, rectangular solids, rings, multi-lobed shapes (e.g., cloverleaf cross section), shapes having multiple holes and "wagon wheels;" preferably spheres. Irregular shapes may also be used.

Preferably, at least 90 wt % of the noble metal(s) is in the outer 70% of catalyst volume (i.e., the volume of an average catalyst particle), preferably the outer 60% of catalyst volume, preferably the outer 50%, preferably the outer 40%, preferably the outer 35%, preferably in the outer 30%, preferably in the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal(s) is within a distance from the surface that is no more than 30% of the catalyst diameter, preferably no more than 25%, preferably no more than 20%, preferably no more than 15%, preferably no more than 10%, preferably no more than 8%. Distance from the surface is measured along a line which is perpendicular to the surface.

Preferably, the noble metal is gold or palladium, preferably gold.

Preferably, the average diameter of the catalyst particle is at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 4 mm, preferably no more than 3 mm. The average diameter of the support and the average diameter of the final catalyst particle are not significantly different.

Preferably, the catalyst is produced by precipitating the noble metal from an aqueous solution of metal salts in the presence of the support. In one preferred embodiment, the catalyst is produced by an incipient wetness technique in which an aqueous solution of a suitable noble metal precursor salt is added to a porous inorganic oxide such that the pores are filled with the solution and the water is then removed by drying. The resulting material is then converted into a finished catalyst by calcination, reduction, or other pre-treatments known to those skilled in the art to decompose the noble metal salts into metals or metal oxides. Preferably, a $C_2$-$C_{18}$ thiol comprising at least one hydroxyl or carboxylic acid substituent is present in the solution. Preferably, the $C_2$-$C_{18}$ thiol comprising at least one hydroxyl or carboxylic acid substituent has from 2 to 12 carbon atoms, preferably 2 to 8, preferably 3 to 6. Preferably, the thiol compound comprises no more than 4 total hydroxyl and carboxylic acid groups, preferably no more than 3, preferably no more than 2. Preferably, the thiol compound has no more than 2 thiol groups, preferably no more than one. If the thiol compound comprises carboxylic acid substituents, they may be present in the acid form, conjugate base form or a mixture thereof. Especially preferred thiol compounds include thiomalic acid, 3-mercaptopropionic acid, thioglycolic acid, 2-mercaptoethanol and 1-thioglycerol, including their conjugate bases.

In one embodiment of the invention, the catalyst is produced by deposition precipitation in which a porous inorganic oxide is immersed in an aqueous solution containing a suitable noble metal precursor salt and that salt is then made to interact with the surface of the inorganic oxide by adjusting the pH of the solution. The resulting treated solid is then recovered (e.g. by filtration) and then converted into a finished catalyst by calcination, reduction, or other pre-treatments known to those skilled in the art to decompose the noble metal salts into metals or metal oxides.

In the method of this invention the process for producing methyl methacrylate (MMA) comprises treating methacrolein with methanol and oxygen in an oxidative esterification reactor (OER) containing a catalyst bed. The catalyst bed comprises the catalyst particles and is situated within the OER such that liquid flow may occur through and around the catalyst bed. Preferably, the catalyst bed occupies only part of the reactor diameter such that reactants circulate around and through the catalyst bed. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101 to 14 MPa); preferably no more than 2000 kPa, preferably no more than 1500 kPa. Preferably, the catalyst bed is in a tubular continuous reactor or a continuous stirred tank reactor, preferably one which contains heat exchange elements such as coils or fins which are utilized to control the temperature of the reactor.

The catalyst particles in the catalyst bed typically are held in place by solid walls and by screens or catalyst support grids. In some configurations, the screens or girds are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. Preferably, the reactor comprises a stack, which is a vertical solid partition having an inside and an outside (i.e., its cross-section perpendicular to the height is a continuous closed curve), allowing liquid flow upward on one side of the stack (e.g., inside or outside) and downward on the other side. In a preferred embodiment the catalyst bed is in the shape of a substantially cylindrical shell located between the stack and the reactor walls. The stack may be a cylindrical shell (cylinder with a cylindrical hole), a rectangular shell or a more complex shape, e.g., a shape derived from a cylindrical shell by flaring the sides outward (toward the reactor walls) at the ends or a shape having an outer or inner surface of a cylindrical shell but with tapering on the other surface to produce a variable thickness; preferably a cross section of the stack perpendicular to the height consists of two or more concentric circles. Preferably, the stack is centered in the reactor. Preferably, the stack is stationary relative to the reactor walls. Preferably, the long dimension of the stack is from 30 to 90% of the long dimension of the reactor, preferably from 40 to 80%. Preferably, the maximum cross-section diameter of the stack is from 40 to 90% of the diameter of the reactor, preferably at least 45%, preferably at least 50%, preferably no more than 85%, preferably no more than 80%. In a preferred embodiment in which the reactor is a continuous stirred tank reactor (CSTR), the height of the stack is from 30 to 80% of the height of the reactor; preferably at least 40%, preferably no more than 75%, preferably no more than 70%. In a CSTR, preferably the height of the catalyst bed is from 30 to 90% of the height of the stack, preferably at least 40%, preferably no more than 80%. Preferably, the sides of the catalyst bed are in contact with the stack. Preferably, the CSTR is configured with the catalyst bed between the stack and the reactor walls with liquid flow downward inside the stack and upward through the catalyst bed. Preferably gaseous reactants and inert (oxygen, nitrogen, carbon dioxide) rise upward through the catalyst bed.

The OER typically produces MMA, along with methacrylic acid and unreacted methanol. Preferably, methanol and methacrolein are fed to the reactor containing the catalyst bed in a methanol:methacrolein molar ratio from 1:10 to 100:1, preferably from 1:2 to 20:1, preferably from 1:1 to 10:1. Preferably, the catalyst bed further comprises inert materials above and/or below the catalyst. Preferred inert materials include, e.g., alumina, clay, glass, silica carbide and quartz. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts. In another embodiment, hydrolysis could be conducted within the distillation column itself.

Preferably, oxygen concentration at a reactor outlet is at least 1 mol %, preferably at least 2 mol %, preferably at least 3 mol %; preferably no more than 7 mol %, preferably no more than 6.5 mol %, preferably no more than 6 mol %. Preferably, the superficial velocity of liquid through the catalyst bed is from 1 to 50 mm/s, preferably at least 2 mm/s, preferably at least 3 mm/s, preferably at least 4 mm/s, preferably at least 5 mm/s; preferably no more than 20 mm/s, preferably no more than 15 mm/s.

A base may be added to the reactor in such a manner as to reduce the formation of adducts which could result from Michael reactions, and to extend the catalyst lifetime. In one preferred embodiment of the invention, no base is added to the reactor, directly or through an external mixing tank.

EXAMPLES

Example #1

The configuration of a CSTR was estimated experimentally by a recycle tubular reactor run at a high recycle rate, which is theoretically identical to a CSTR with the same recycle ratio. A run was conducted in which 20 wt % methacrolein, 200 ppm inhibitor, and a balance of methanol were fed to a ⅜" (9.5 mm) stainless steel tubular reactor containing a short front section of silica carbide followed by 10 g of catalyst. The catalyst consisted of 1.5 wt % Au on a Norpro 1 mm diameter high surface area alumina spherical support. A gas containing 8% oxygen in nitrogen was also feed to the reactor. The reactor was operated at 60° C. and 160 psig (1200 kPa). The product of the reactor was sent to a liquid-vapor separator and the vapor was sent to a condenser with liquid return. A portion of the product stream from this separator was recycled to the reactor inlet and combined with the feed entering the reactor. Results are described in the table below. MIB is reported in ppm on a 100% MMA product basis. Product MMA is the percent MMA among products originating as methacrolein reactant.

| Feed (g/hr) | recycle (g/hr) | Gas (sccm) | Gas Type | Prod MMA (wt %) | Conv (%) | STY (m/Kg cat. hr) | MIB (ppm) |
|---|---|---|---|---|---|---|---|
| 20 | 180 | 380 | 8% $O_2$ | 97.8 | 63 | 3.2 | 480 |

The invention claimed is:

1. A method for preparing methyl methacrylate from methacrolein and methanol; said method comprising contacting in a reactor a mixture comprising methacrolein, methanol and oxygen with a heterogeneous catalyst comprising a support and gold, wherein said catalyst has an average diameter of at least 300 microns and at least 90 wt % of the gold is in the outer 70% of catalyst volume, wherein oxygen concentration at a reactor outlet is from 0.5 to 7.5 mol % and wherein the reactor comprises a partition with the catalyst bed on a first side of the partition and with flow through the catalyst bed in a first direction and flow on a second side of the partition in an opposite direction.

2. The method of claim 1 in which the catalyst bed is in the shape of a cylindrical shell located between the partition and the reactor walls.

3. The method of claim 2 in which the catalyst has an average diameter from 400 microns to 10 mm.

4. The method of claim 3 in which the catalyst bed is at a temperature from 40 to 120° C.

5. The method of claim 4 in which the reactor is a continuous stirred tank reactor and height of the partition is from 30 to 90% of height of the reactor.

6. The method of claim 5 in which the continuous stirred tank reactor is configured with liquid flow downward inside the partition and upward through the catalyst bed.

7. The method of claim 6 in which at least 90 wt % of the gold is in the outer 60% of catalyst volume.

8. The method of claim 1 in the support is selected from the group consisting of titania or γ-, δ-, or θ-alumina.

9. The method of claim 8 in which at least 95 wt % of the gold is in the outer 50% of catalyst volume.

* * * * *